(12) United States Patent
Sinkfield et al.

(10) Patent No.: US 11,898,774 B2
(45) Date of Patent: Feb. 13, 2024

(54) MISTING SYSTEM WITH REMOVABLE CANOPY AND USER ACTUATED CONTROL WITH OPTIONAL MODULAR CONSTRUCTION

(71) Applicant: SINKFIELD AND HART ENTERPRISES, L.L.C, Miami, FL (US)

(72) Inventors: Joseph Sinkfield, Miami, FL (US); C. Brian Hart, Miami, FL (US); Robert C. Kain, Sr., Maggie Valley, NC (US)

(73) Assignee: SINKFIELD AND HART ENTERPRISES, L.L.C., Miami, FL (US)

( * ) Notice: Subject to any disclaimer, the term of this patent is extended or adjusted under 35 U.S.C. 154(b) by 0 days.

(21) Appl. No.: 18/103,792

(22) Filed: Jan. 31, 2023

(65) Prior Publication Data

US 2023/0194109 A1 Jun. 22, 2023

Related U.S. Application Data

(62) Division of application No. 17/558,145, filed on Dec. 21, 2021, now Pat. No. 11,598,538.

(51) Int. Cl.
*B05B 9/00* (2006.01)
*F24F 6/14* (2006.01)
*B05B 9/04* (2006.01)

(52) U.S. Cl.
CPC .............. *F24F 6/14* (2013.01); *B05B 9/007* (2013.01); *B05B 9/0403* (2013.01); *F24F 2006/146* (2013.01); *F24F 2221/125* (2013.01)

(58) Field of Classification Search
CPC ...... Y02B 30/54; F24F 6/14; F24F 2006/146; F24F 2221/38; B05B 9/007; B60H 1/00264

See application file for complete search history.

(56) References Cited

U.S. PATENT DOCUMENTS

| 5,226,438 A | * | 7/1993 | Dubinsky | A45B 15/00 135/33.4 |
| 5,330,104 A | * | 7/1994 | Marcus | F24F 1/0007 239/266 |
| 5,598,719 A | * | 2/1997 | Jones | B05B 7/0075 62/304 |
| 5,776,015 A | * | 7/1998 | Bernhardt | G01C 3/22 473/407 |

(Continued)

*Primary Examiner* — Joseph A Greenlund
(74) *Attorney, Agent, or Firm* — The Concept Law Group, P.A.; Robert C. Kain, Jr.; Scott D. Smiley

(57) ABSTRACT

The misting system has, in one embodiment, two seats with misting heads above each seat. A platform supports the seats, a tank, a pump and a power source. A supply line couples the tank-supplied pump and the misters. Removable canopy is mounted above seats by vertical and curvaceous struts and the misters are mounted on the struts. A user actuated UA control on the seat(s) activates pump ON to release mist. Wheels make the module mobile. Battery, solar power, and chiller are options. A countdown timer turns OFF the pump or controllable, inline valves after initial activation of the UA control. A level sensor in the tank alerts the user via a user display. A pressurized system can be used. Multiple modules coupled together are controlled by a master module with master controls.

10 Claims, 8 Drawing Sheets

(56) References Cited

U.S. PATENT DOCUMENTS

| | | | | |
|---|---|---|---|---|
| 6,112,538 A * | 9/2000 | Strussion | F04B 43/026 | 62/304 |
| 6,151,907 A * | 11/2000 | Hale | B60H 1/00407 | 62/304 |
| 6,325,362 B1 * | 12/2001 | Massey | B60H 1/3202 | 261/78.2 |
| 6,393,857 B1 * | 5/2002 | Malueg | B05B 1/207 | 62/239 |
| 6,886,759 B1 * | 5/2005 | Okronick | A45B 3/00 | 239/289 |
| 7,150,162 B1 * | 12/2006 | Brunner | F24F 5/0035 | 280/658 |
| 7,334,744 B1 * | 2/2008 | Dawson | A01G 13/065 | 239/200 |
| 7,497,225 B1 * | 3/2009 | Klein, Jr. | A45B 3/00 | 135/118 |
| 7,497,255 B2 | 3/2009 | Klein, Jr. et al. | | |
| 8,753,216 B2 * | 6/2014 | Hsieh | B05B 1/20 | 472/116 |
| 8,881,998 B1 * | 11/2014 | Sinkfield | A01K 1/0082 | 239/128 |
| 9,750,318 B2 * | 9/2017 | Rao | A45B 25/06 | |
| 9,859,748 B2 * | 1/2018 | Wang | H01L 31/042 | |
| 10,753,627 B1 * | 8/2020 | Stevenson | F24F 7/065 | |
| 10,905,536 B2 * | 2/2021 | Neupert | B05B 7/2491 | |
| D912,203 S * | 3/2021 | Andersen | C10J 3/845 | D23/213 |
| 11,008,030 B2 * | 5/2021 | Cohen | B62B 5/0083 | |
| 11,293,651 B1 * | 4/2022 | Wang | F24F 8/22 | |
| 11,598,538 B1 * | 3/2023 | Sinkfield | B05B 9/007 | |
| 2003/0213257 A1 * | 11/2003 | Madrid | B60H 1/3202 | 62/304 |
| 2005/0082390 A1 * | 4/2005 | Ferrono | B60H 1/3202 | 239/332 |
| 2007/0089448 A1 * | 4/2007 | Critchfield | B60H 1/3202 | 62/304 |
| 2008/0006263 A1 * | 1/2008 | Seichei | F24F 5/0035 | 62/331 |
| 2008/0048051 A1 * | 2/2008 | Chang | F24F 6/14 | 239/289 |
| 2008/0265611 A1 * | 10/2008 | Flynn | B60J 7/1226 | 296/108 |
| 2009/0090404 A1 * | 4/2009 | Kuelbs | A45B 25/14 | 135/16 |
| 2010/0230514 A1 * | 9/2010 | Meadors, Jr. | B60R 3/022 | 239/337 |
| 2010/0276513 A1 * | 11/2010 | Huff | A01G 25/09 | 239/266 |
| 2011/0146319 A1 * | 6/2011 | Branning | A47B 13/00 | 108/50.13 |
| 2011/0174448 A1 * | 7/2011 | Haagenson | B60J 5/0487 | 160/124 |
| 2011/0226870 A1 * | 9/2011 | Rotunda | B60H 1/3202 | 135/88.01 |
| 2013/0098079 A1 * | 4/2013 | Apolony | F24F 5/0035 | 261/78.1 |
| 2013/0168882 A1 * | 7/2013 | Lykins | F04D 29/705 | 220/592.2 |
| 2014/0232147 A1 * | 8/2014 | Held | B60Q 1/2611 | 296/210 |
| 2015/0144165 A1 * | 5/2015 | Rao | A45C 13/40 | 135/16 |
| 2016/0326765 A1 * | 11/2016 | Barbret | E04H 15/02 | |
| 2017/0332750 A1 * | 11/2017 | Gharabegian | F24S 50/20 | |
| 2018/0049523 A1 * | 2/2018 | Zadie | E04H 12/22 | |
| 2018/0266714 A1 * | 9/2018 | Perrelle | F04D 25/084 | |
| 2019/0291539 A1 * | 9/2019 | Gordon | B60H 1/30 | |
| 2019/0357643 A1 * | 11/2019 | Pan | A45B 25/00 | |
| 2021/0022465 A1 * | 1/2021 | Grabon | F24F 13/04 | |
| 2021/0030125 A1 * | 2/2021 | Grabon | F24F 5/0035 | |
| 2021/0030126 A1 * | 2/2021 | Grabon | F24F 13/02 | |
| 2021/0033294 A1 * | 2/2021 | Grabon | F28C 1/00 | |
| 2021/0048218 A1 * | 2/2021 | Grabon | F24F 6/12 | |
| 2021/0054647 A1 * | 2/2021 | Grabon | F24F 5/0035 | |
| 2021/0138875 A1 * | 5/2021 | Oyler | F04D 25/166 | |
| 2021/0156577 A1 * | 5/2021 | Li | B01F 23/2133 | |
| 2021/0316806 A1 * | 10/2021 | Perlo | B62J 9/10 | |
| 2022/0105904 A1 * | 4/2022 | Akabayashi | B05B 15/654 | |
| 2023/0194109 A1 * | 6/2023 | Sinkfield | B05B 13/0278 | 297/180.15 |

* cited by examiner ns. Another feature includes power sources such as a
MISTING SYSTEM WITH REMOVABLE CANOPY AND USER ACTUATED CONTROL WITH OPTIONAL MODULAR CONSTRUCTION This is a divisional patent application based upon and claiming the benefit of application Ser. No. 17/558,145, filed Dec. 21, 2021, the contents of application Ser. No. 17/558,145 is incorporated herein by reference thereto.

FIELD OF THE INVENTION

The present invention relates to a misting system adapted to release aerosolized water above and about seated users. A removable canopy, is deployed above the seats. A user actuated (UA) control activates the release of aerosolized water.

BACKGROUND OF THE INVENTION

Athletes and individuals during an athletic activity often times experience extreme heat when the activity is conducted in a hot climate. In order to reduce his or her body temperature, these athletes and individuals may be bombarded by aerosolized water or mist. U.S. Pat. No. 8,881,998 to Sinkfield discloses a portable misting trailer system for preventing bodies from overheating and a system for regulating body temperature. The '998 patent discloses a series of hoops or ribs carried by a trailer. The trailer also includes a water storage tank, a pump and a power source, which is typically one or more batteries. The rear region of the trailer has a plurality of misting heads mounted on the hoops or ribs such that and athletes or and individual may stand or sit in this rear region and be bombarded by aerosolized water or mist.

Although the misting trailer disclosed in the '998 patent is useful, it is sometimes difficult to place the trailer-carried misting system on the playing field or court where the athletes or individuals engage the strenuous activity.

Therefore, a need exists to overcome problems with the prior art.

SUMMARY OF THE INVENTION

The invention provides a misting system with a removable canopy and user actuated (UA) controls with an optional modular construction.

In accordance with one of the several features of the present invention, embodiments of the present invention include a misting system with at least two seats adapted to provide seating for one or more seated persons subject to the aerosolized water proximally released above and about the seats. A platform supports the seats and a water tank is carried by the platform. A pump is coupled to the tank. The misting system also includes an electrical power source coupled to the pump. At least one supply line is coupled at one end to an output of the pump and, at the opposite and, to an aerosolizing misting head. A removable canopy is removably mounted above the platform on at least one extendable vertical strut element. Also, the misting system includes at least one curvaceous strut element coupled to the vertical strut. In a further embodiment, several curvaceous strut elements are utilized along with a curvaceous framework to support the removable canopy. The misting head and the water supply line is mounted either on the curvaceous strut element or the extendable vertical strut element. A user actuated (UA) control is on or adjacent one or more of the seats. The UA control activates the pump ON thereby coupling the electrical power source to the pump. Once the pump is ON, water is supplied by the supply line to the misting head thereby releasing a mist or aerosolized water proximately above and about persons in one or the other or both of the platform seats.

In accordance with a further feature of the present invention, the seats have a common adjoining wall. Also, the platform may have a pair of wheels rotatably mounted beneath the platform, thereby permitting the platform, as well as be supported misting system elements, to be moved. In one embodiment, the wheels are disposed below the platform at a rearward location.

In accordance with the present invention, the UA control is either a manual control, adapted to be turned ON by seated persons, or is a seat sensor activated when the person sits on the seat.

In accordance with yet another feature, the canopy is removable with a plurality of releasable detachment mechanisms. Another feature includes power sources such as a rechargeable battery, a solar panel coupled to a complementary battery, and a removable rechargeable battery mounted in a battery containment, all supported by the platform. Further, the platform, in another embodiment, is not movable. Other features which may be incorporated into the misting system include a water chiller in the water supply line, typically downstream of the pump, or a water heater. Further, the UA control may include a countdown or a timing function to turn OFF the pump after an initial activation of the UA control. A further refinement of the invention would include a water level sensor in or associated with the water tank to generate a water level signal. A controller is electronically coupled to the level sensor. The controller further has a user display (UD) interface visually presenting a low water alert based upon the water level signal.

In accordance with yet another embodiment of the invention, a pressurized misting system is utilized. This system has two seats supported by a platform, a water tank (also supported by the platform), and a pump fluidly coupled to the tank. In water supply line connects the pump to one or more misting heads. There is a controllable valve in the water supply line. The pump has a pump control to maintain a predetermined or preset pressure in the supply line. The removable canopy is mounted above the platform by the vertical strut element (not necessarily extendable) and one or more curvaceous strut elements. The curvaceous strut element or elements extend above and partly over the seats. The misting head is mounted on either the curvaceous strut or the vertical strut. The user actuated UA control is on or adjacent one, or the other, or both seats, and is electrically coupled to the controllable valve. This UA control activates the valve OPEN when the UA control is activated ON by one or the other of the persons seated on the module. The result being the pressurized water is supplied through the supply line and the valve is open to the misting head thereby releasing water mist above and about the seats. Similarly, the UA control could be either manual or seat-activated. The canopy is detachable by releasable detachment mechanisms (such as snaps, hooks, loops, fabric ties, tiedowns, or tongue and groove attachments).

In another embodiment, a modular misting system is disclosed. This modular misting system includes a master module and a slaved module. The master module has one or more seats, a water tank, a pump controlled by a master pump control, and an electrical power supply source supported by the platform. A water supply line is coupled to the pump and to one or more misting heads. These misting heads are mounted on either a vertical strut or a curvaceous strut. A master controllable valve in the supply line is controlled by a master valve control command (in distinction to the master pump control). A master UA control on or adjacent the master seat is electrically coupled to the pump and the master valve. The master UA control activates the pump ON with the master pump control and the master valve control is activated OPEN when the UA control is activated ON by the corresponding seated person thereby releasing the mist. The slave module has a slaved-mounted seat supported by a slaved platform. A slaved water supply line has a slaved input at one end and, at its other end, a misting head. The slaved water supply line includes a controllable slaved valve. A slaved UA control is also mounted on one or the other of the slave-mounted seats. The slaved UA control activates the pump ON (via the master module) with the master pump control and the slaved valve control OPEN (on the slaved module) when the slaved UA control is activated ON by the respective person in the slave-mounted seat, and, in the absence of any person in any slaved-mounted seat, either the slaved UA control or the master UA control activities the slaved valve control CLOSED. The master module and the slave module are detachably coupled together by (i) a detachable water line coupler between the pump and the slaved misting head, and (ii) a detachable control line coupler between the slaved UA control and the slaved valve. Of course, the slaved module may include slaved control lines extending to the controllable slaved valve. These slaved control lines can be interconnected to the master controller by the detachable control line coupler.

A further enhancement of the modular system includes the feature that the master UA control is either a manual control turned ON by the seated person or a seat sensor. The slave UA control is also either a manual or a seat-sensitive control point. As described above, the canopies on the master and/or slave modules are releasably detachable. The electrical power source on the master module can be a rechargeable battery, a solar panel with a backup battery, and a removable rechargeable battery, all mounted on the master platform.

Another enhancement to the modular system includes a master controller electrically coupled to the pump and the master UA control (all in the master module). The master controller has a countdown timer function or a time-OFF clock function, to turn OFF the master pump control after an initial activation of the master pump control ON by either the master UA control or the slave UA control. The time-out function can also be used to CLOSE the controllable in-line valves, in the same manner as the pump. When used with a chiller on the master module, the controller has a chiller ON function, dependent upon the initial activation of the master pump control ON, and a chiller OFF function, dependent upon a chiller countdown timing function which is a function in the master controller. As discussed earlier, the master module may detect the level of water in the mounted tank by a water level sensor. The master controller, in the master module, also includes a user display UD visually presenting a low water alert based upon the water level signal from the level sensor.

In another embodiment of the present invention, a master misting module is provided. This master module controls mist developed by a slaved misting module. The master module includes a detachable coupling for removably coupling the master module to the slave module. The detachable coupling is one of a water supply coupling and a control line for activating a valve-controlled slaved-mounted mister, or a water supply coupling, a slaved seat-sensing control line, and the control line for activating a valve controlled slaved-mounted mister. The master module has a master seat supported by a master platform. The master seat provides seating for a person subject to the mist generated by misting heads. The master module also includes a water tank and a pump controlled by a master pump control. An electrical power source is supported by the platform and is coupled to the pump. A water supply line is coupled, at one end, to the output of the pump and, at an opposite end, to a master misting head. A master controllable valve, inline the water supply line, is controlled by a master valve control. The canopy is mounted above the master platform by at least one vertical strut and at least one curvaceous strut. The curvaceous strut extends partly over and above the master seat. The misting head is mounted either on the curvaceous strut or the vertical strut and is fluidly connected to the supply line. A master user actuated control is on or adjacent the master seat and is electrically coupled to the pump and the master valve. The master user actuated UA control activates the pump ON with the master pump control command and activates the master valve OPEN with the master valve control command when the UA control is activated ON by the seated person. In the absence of a seated person, the master UA control activates the master valve control CLOSED. Further, upon activation of the control line for the slave-mounted mister or the slave seat-sensing control line, the master controller activates the pump ON with the master pump control command and hydraulically couples the pump to the slave-mounted mister via the water supply coupling. The master controller opens the slaved inline valve.

Although the invention is illustrated and described herein as embodied in a misting system with a removable canopy and user actuated (UA) control with an optional modular construction, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

In the description of the embodiments of the present invention, unless otherwise specified, azimuth or positional relationships indicated by terms such as "up", "down", "lateral" or to the "left" or "right", "inside", "inboard", "outside", "outboard", "front", "forward," "back", "rear," and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "mounted", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

In this document, the term "lateral" should be understood to mean in a direction corresponding to a direction which is about 90 degrees to the referenced axis of the referenced item. For example, a misting head is laterally disposed on a curvaceous strut and is normal or generally perpendicular to the run of the strut. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, an App operable with a control server, a source code, an object code, a shared library/dynamic load library and/or other sequence of instructions designed for execution on a computer system. Those skilled in the art can understand the specific meanings of the above-mentioned terms in the embodiments of the present invention according to the specific circumstances.

BRIEF DESCRIPTION OF THE DRAWINGS

Further objects and advantages of the present invention are set forth in the detailed description below and the accompanying figures, where like reference numerals refer to identical or functionally similar elements throughout the separate views and which, together with the detailed description below, are incorporated in and form part of the specification, and which serve to further illustrate various embodiments and explain various principles and advantages all in accordance with the present invention.

DETAILED DESCRIPTION OF THE INVENTION

Figure 1A:
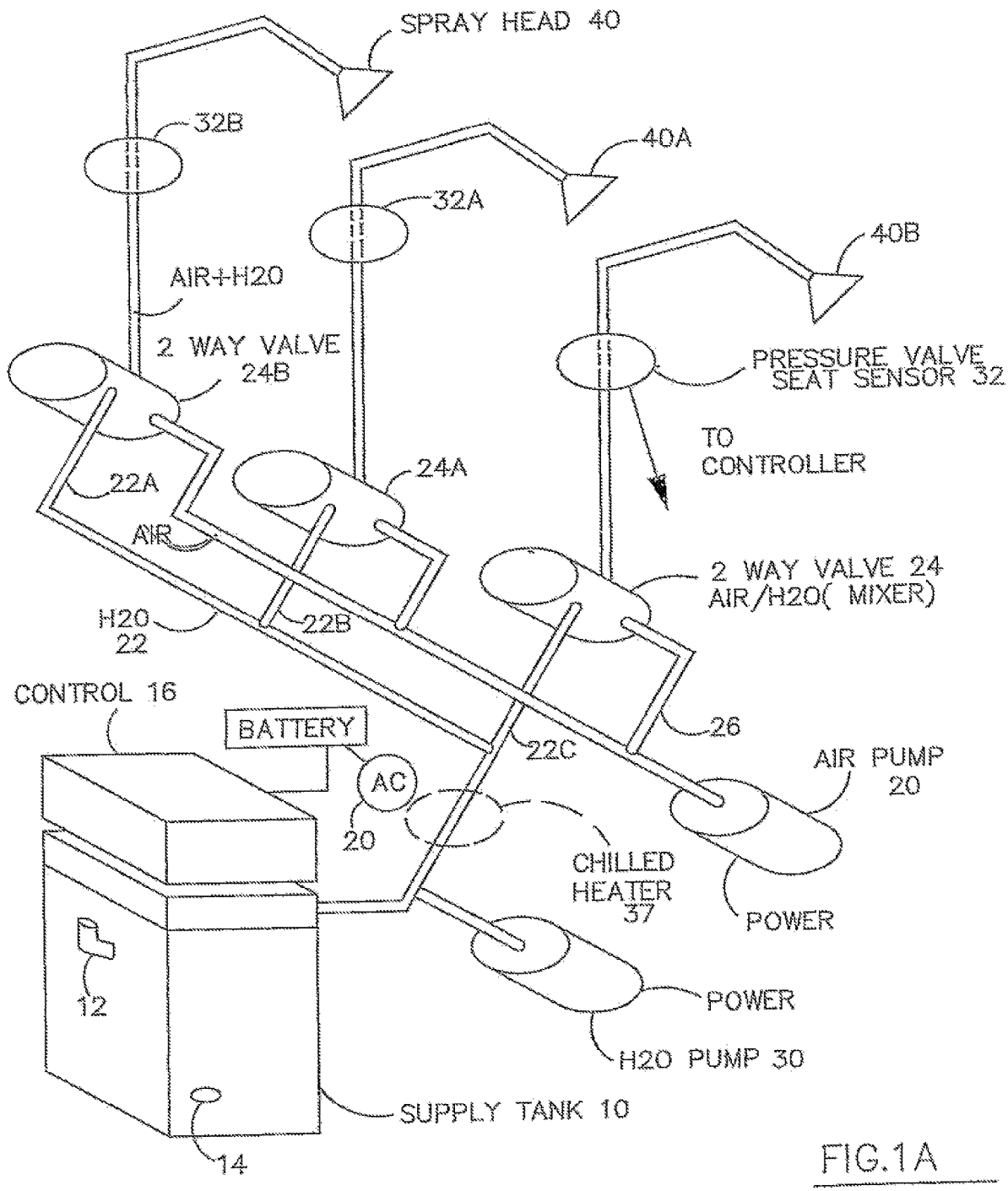
FIG. 1A diagrammatically illustrates a hydraulic and pneumatic schematic of an embodiment of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient misting system with a removable canopy and user actuated (UA) control with an optional modular construction.

Figure 1B:
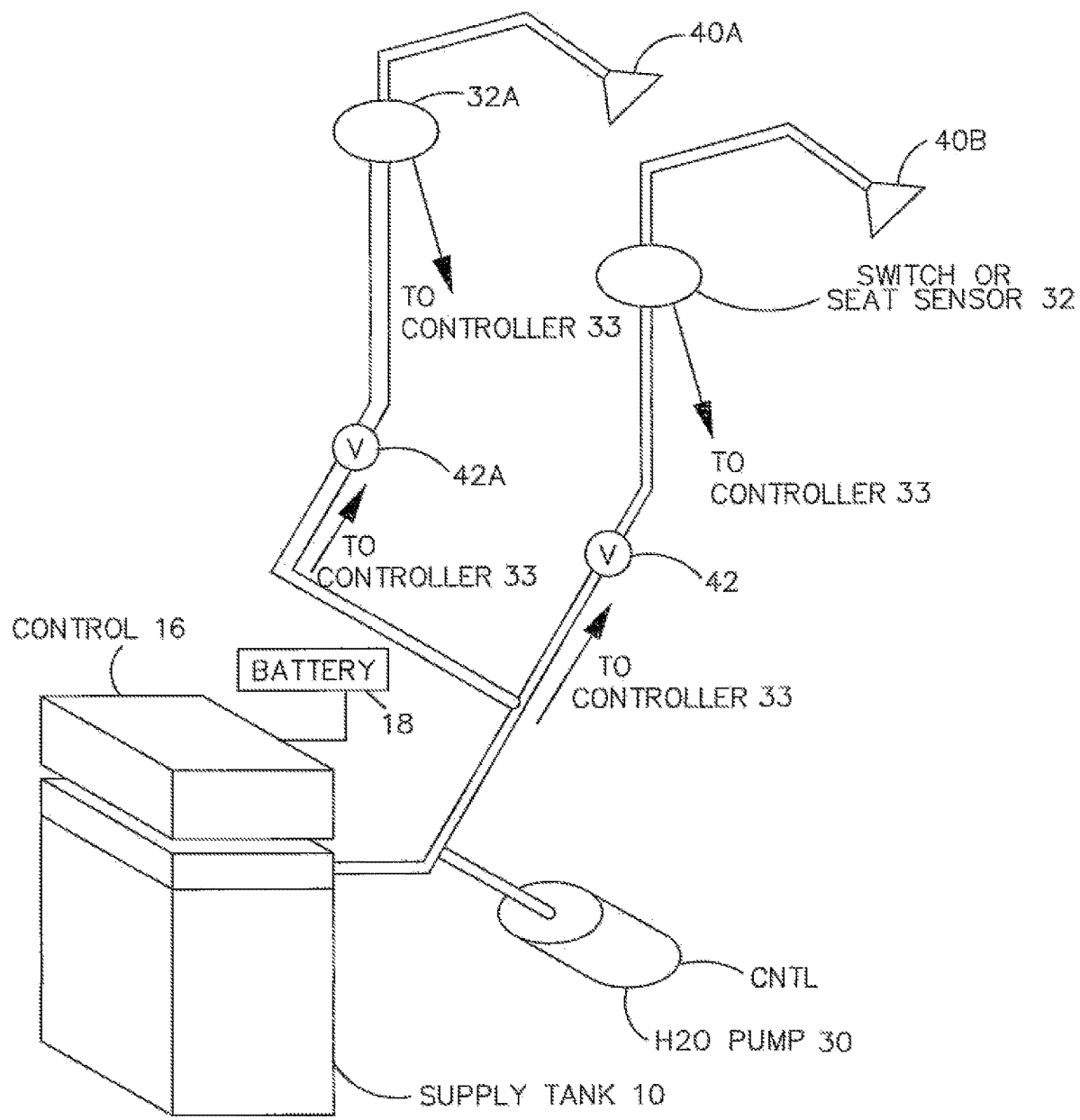
FIG. 1B diagrammatically illustrates another hydraulic and schematic of an embodiment of the present invention.

FIG. 1A diagrammatically illustrates a hydraulic and pneumatic schematic of an embodiment of the present invention. FIG. 1B diagrammatically illustrates another hydraulic and pneumatic schematic of another embodiment of the present invention. In FIG. 1A, a water supply tank includes a fill port 12 and a drain port 14. A control system 16 is supplied, in a preferred embodiment, by onboard battery 18 which, in a preferred embodiment, is rechargeable from an AC power source 20. Water from supply tank 10 is carried by water supply lines 22, 22A, 22B, and 22C. These water supply lines are fed into respective two-way valves which mix supplied air with the water. These mixing valves 24, 24A, and 24B are also supplied with air via pneumatic supply line 26. An air pump 28 provides pressurized air to the mixing valves. Water is supplied to the water supply line 22 by a water pump 30. Power is supplied to air pump 28 and water pump 30. As is known in the art, the power may also include both a power supply and a control signal for the operation of the water pump and/or air pump. Alternatively, a separate control line could be used to control these pumps.

The output of mixing valves 24, 24A, 24B, is controlled by a respective pressure valve or seat sensor 32, 32A, 32B. Seat sensor 32 may be any type of sensor such as a pressure sensor, activated when the user sits on the seat subject to the delivery of the water mist, or a sensor activated by a change in resistance caused by the user sitting in or on the seat, a capacitive activated sensor, or a light activated sensor. The seat sensor 32 generates a control signal ("CNTL") indicating the presence, and the absence, of a user on the seat. This user activated control is delivered to controller 16 and, in some situations, controller 16 then powers ON water pump 30 and air pump 28. Sensor 32 may generate the pump ON signal as a user activated UA control command.

In a pressurized misting system, once controller 16 determines that a proper pressure is maintained at valves 24, controller 16 opens the valves and hence delivers aerosolized water via spray misting heads 40, 40A, 40B to the user seated on the platform. In the pressurized system, an inline pressure sensor would be monitored by the display-controller 16 to maintain the water pressure in the supply line. Alternatively, in a pressurized system, the pump may be turned ON until a predetermined pressure is obtained in the supply line, then the in-line control valves would be turned ON or open therefore releasing mist form the spray heads.

Optionally, the system may include a chiller and or a heater 37 located downstream water supply tank 10, that is, upstream or downstream water pump 30. More efficiently, that heater or the chiller 37 would be located downstream water pump 30. The chiller 37 is optional because water supply tank may have a closable lid which, when opened, can accommodate the delivery of ice into supply tank 10.

Figure 2:
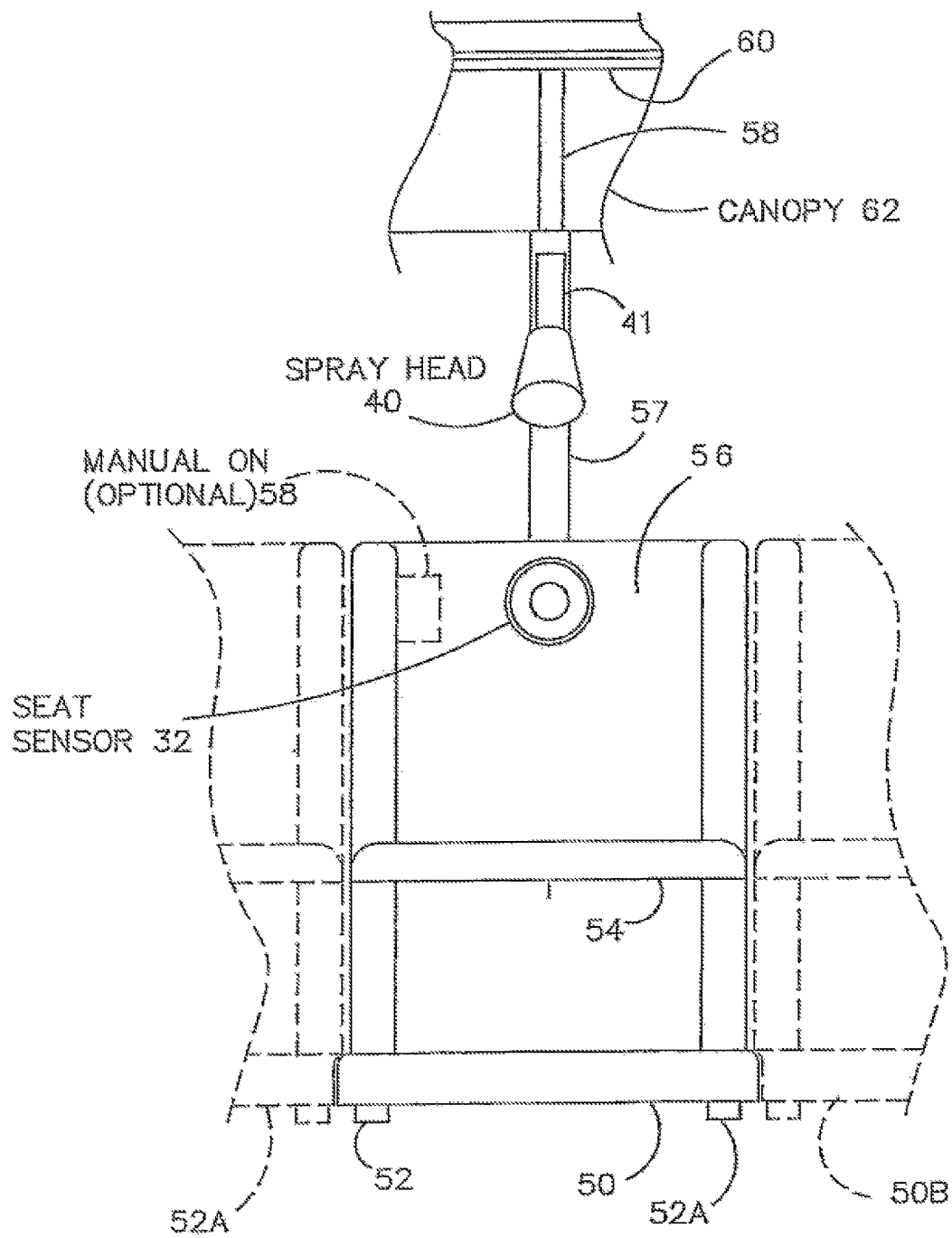
FIG. 2 diagrammatically illustrates a fragmentary front view of the invention showing the seat for the user, athlete, or individual subject to the aerosolized mist.

FIG. 1B diagrammatically illustrates another embodiment of the invention and FIG. 2 diagrammatically illustrates a fragmentary front view of the invention showing the seat for the user athlete or individual subject to the aerosolized mist. In the most simplified embodiment of FIG. 1B, control 16 determines when one or the other of the seat sensors 32, 32A generates control signals. Control 16 activates pump 30 ON thereby pumping water through supply lines 22 to spray heads 40, 40A. As discussed later, the modular system is a two-seater misting system and, when either seat sensor 32 or seat sensor 32A is activated ON, control 16 turns the pump 30 ON thereby supplying water to both misting heads 40, 40A. In a more complex embodiment, controller 16 activates pump 30 ON and maintains water pressure in supply lines 22. When no user occupies a seat, and when the seat sensors at both user seats are OFF, valves 42, 42A are maintained in a CLOSED or OFF condition. Similarly, the pump is OFF due to the absence of any control commands for the UAs in or on the seats. When either one or the other seat sensor 32, 32A is activated ON, control 16 applies the appropriate control signal to one or the other or both of valves 42, 42A, thereby activating these valves OPEN or ON. The result being that water is supplied to spray heads 40, 40A. In a different control configuration, when using independent seat UA controls, single misting head is programmed ON based upon a single seat sensor, such as seat sensor 32, which issues a control ON signal to control 16, resulting in valve 42 being activated ON or OPEN to deliver water only to misting head 40. A pressurized line system with independent flow valves 42, 42A, permits independent operation and delivery of misting water output to a respective spray or misting head 40, 40A.

It is well known that spray head 40, when supplied with water, can generate mist or aerosolized water as an output. See U.S. Patent Pub No. 20090242665; U.S. Pat. Nos. 4,925,097; 6,651,901; and U.S. Patent Pub No. 20080210772.

FIG. 2 shows an optional manual UA control 58 rather than, or in addition to sent UA sensor 32. Sent 54 is supported by platform 50. Wheels 52, 52A permit platform 50 to be moved. Laterally disposed modules 50A, 50B are shown. Sent back 56 supports the user.

Figure 3:
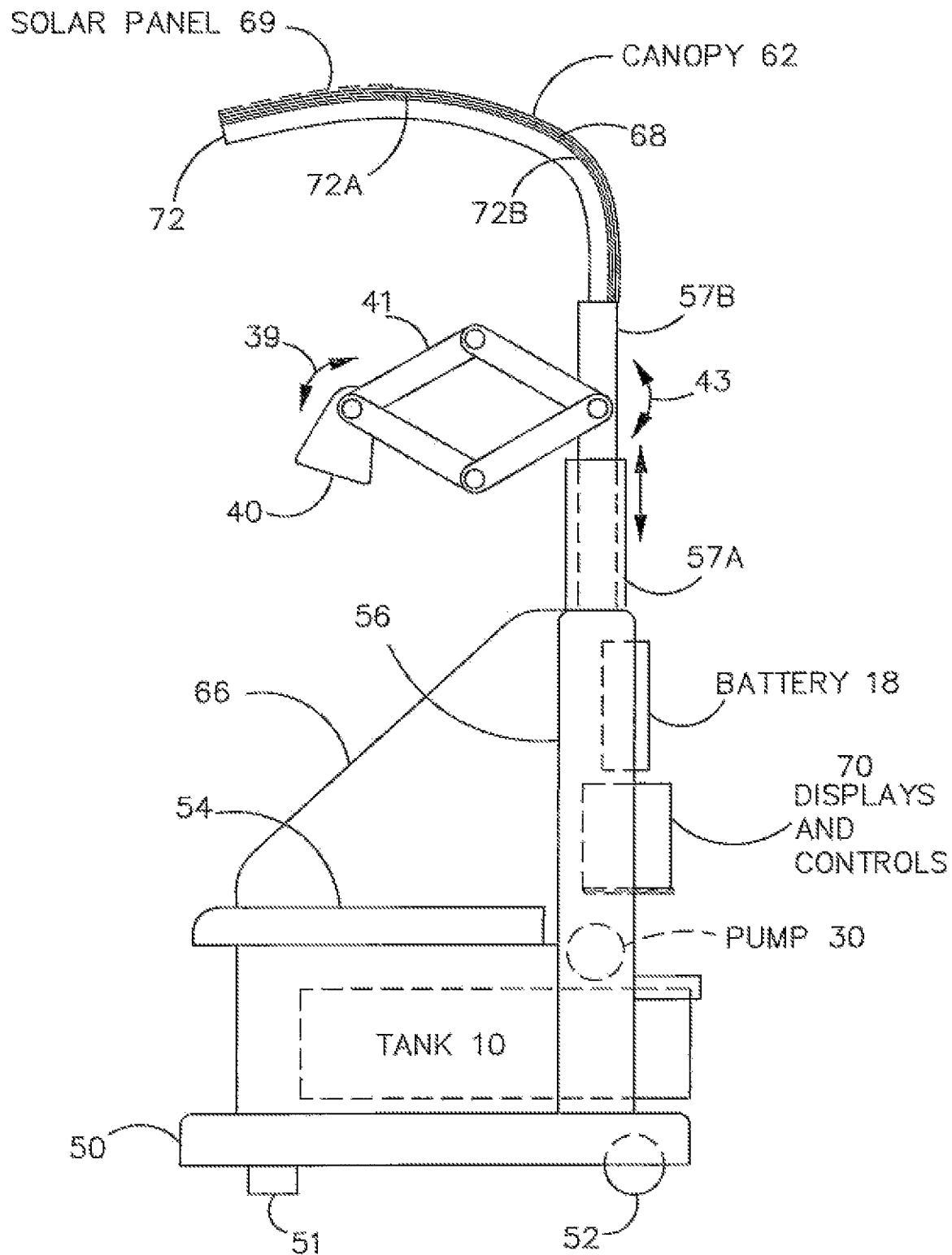
FIG. 3 diagrammatically illustrates a side elevational view of a portion of the seat for the athlete or individual, the removable canopy, optional solar panel, and possible location of the control panel and monitor displays, on-board power source, and water tank.

FIG. 3 diagrammatically illustrates a side elevational view of a portion of the seat for the athlete or individual, the removable canopy, an optional solar panel, and possible location of the control panel and monitor displays, an on-board power source and water tank. In FIG. 3, a single seat 54 is shown to support the user or athlete (not shown) below misting spray head 40. Although the preferred embodiment is two-seater system (see FIG. 5), the system may be configured as a single seat, or three, four or five seats as per the manufacturer's specifications. Seat 54 is mounted and supported by a platform 50. The platform is movable by at least a pair of wheels 52, 52A. As shown in FIG. 3, these wheels may be rotatably mounted at a rearward location on platform 50. To maintain the platform in a relatively level position, the two wheeled system would include stubs 51 on the front of the platform as shown in FIG. 3. Alternatively, the platform may have four wheels, a pair of rearward wheels and a pair of forward wheels. The term "forward" referring to a position wherein the user would approach and sit on seat 54. Another embodiment of the present invention is a stationary misting station with one or more non-movable platforms.

In one embodiment, seat sensor 32 is located either on the horizontal section of seat 54 or ON the vertical back section 66 of seat 54 as shown in FIG. 2. Optionally, the misting system may have a manual ON control 58 to either replace seat sensor 32 or to supplement seat sensor 32. As explained later, the seat sensor 32 enables controller 16 to have a time-out function such that within a predetermined time after seat sensor 32 is activated ON, controller 16 turns OFF the pump 30 or closes valve 42 thereby stopping the delivery of mist from head 40.

Spray head 40 is mounted above seat 54 on a spray head strut 41. Spray head strut 41 is, in turn, mounted on either vertical strut 56 or on curvaceous strut 58. In one embodiment, canopy 62 is mounted on curvaceous strut 58 and a laterally extending canopy strut 60 shown in FIG. 3 (lateral compared to the front and rear dimensions). Spray or misting head 40 represents one or more spray misting heads on the singular water supply line leading to the heads. The heads may be attached anywhere on the supply line.

In the modular configuration shown in FIG. 2, one or more misting seat modules 50A, 50B can be connected mechanically, hydraulically and with coupled command-carrying cables or lines such that the owner of the misting system can build-out a misting system with multiple misting seats.

FIG. 3 diagrammatically illustrates a side elevational view of a portion of the seat for the athlete or individual, the removable canopy, optional solar panel, and possible location of the control panel and monitored displays, on board power source and water tank. Although FIG. 3 diagrammatically shows display and control panel 70 and battery 18 in certain positions on the backside of seat 54, a person of ordinary skill in the art could locate the control and display panel at any other convenient location including in the side panel 66 or side wall thereby permitting either the user or a manager to see the display, see certain operational conditions, and to enable or disable certain controls as discussed later. Further, battery 18 may be located at a different location supported by platform 50. Battery 18, as shown in FIG. 3, is removable such that it can be removed and recharged as needed. If a solar panel 69 is utilized, a solar panel converter would be interposed at the output of the solar panel such that the batteries would be recharged while the panel is activated.

In this illustrated embodiment, seat 54 has a vertical divider panel 66 on one lateral side of seat platform 54. Other seat configurations may be selected by the manufacturer. Hence, each module may be a single seat module, a two-seater, three-seater, etc. In the master-slave system described herein, it is likely the master module will have two seats due to the water tank size, control systems and onboard power. It is believed that the onboard power is needed because (a) the location of an AC outlet on or about a playing field is uncertain; (b) the misting system can be located anywhere about the playing field; and (c) the electrical power requirements of the system are relatively low.

Canopy 62 is removable from curvaceous canopy supporting strut 58 (See FIG. 3) as noted by detachable elements 68. In one embodiment, a plurality of manual releasable detachment mechanisms is intermediate the removable canopy 62 and the curvaceous strut element 58. The manually releasable detachment mechanisms may be a snap element, a hook and a loop (such as VELCRO™), a button and a complementary buttonhole, a fabric strap, a fabric strap bearing micro-hooks cooperative with complementary cloth bearing micro-loops (VELCRO™ attachment), a fabric tether, a tongue operative in a groove, a snap, and a tiedown. Other detachable and releasable mechanisms are known to persons of ordinary skill in the art.

The purpose of a removable canopy is one of the several important inventive features. First, the removable canopy can be removed from the misting system and cleaned. Since the canopy is typically deployed in an outside environment, it is subject to accumulated dust, dirt and mold. Hence, the canopy should be removable to clean the fabric. Second, a removable canopy permits the user to extend the canopy to its terminal edge 72 or some intermediate location 72A or 72B. When canopy 62 is that terminal strut position 72, maximum shade is developed for an athlete or a user on seat 54. In a partly deployed position when the terminal end of canopy 62 is at intermediate detachment point 72A, partial shade is established for the user on seat 54. Likewise, when the terminal end of canopy 62 is at inboard detachment position 72B, only a slight bit of shade is established for the user on seat 54. Third, canopy 62 can be imprinted with the name of the athlete team and/or carry an advertisement. Since the mobile misting station can be positioned at various locations on the playing field or court, it is important that the misting station be moved to permit maximum view ability of the playing field or court without obstructing the view of visitors watching the athletic activity. Since the removable canopy can be imprinted with an advertisement, the advertiser can pay for one or more mobile misting stations. This economically benefits the misting system owner.

FIG. 3 also shows that misting head 40 can be rotated in the direction shown by double-headed arrow 39 to better present the mist to a user seated on seat 54. In the illustrated embodiment, misting head 40 is mounted on one side of a head support strut system 41. Head support system 41 is also mounted on vertical strut 56. As shown by the double-headed arrow 43, the misting strut system 41 rotates with respect to vertical strut 56. In addition, FIG. 3 shows vertical strut 56 with two vertically adjustable segments, vertical strut segment 57A and vertical strut segment 57B. The vertical struts 57A, 57B permit the modular misting system to be vertically collapsed. See double headed vertical arrow. FIG. 3 does not show water supply lines coupling misting head 42 to pump 30 and tank 10. The supply lines would run in and about vertical strut system 57A, 57B as well as through some connection with head supporting strut system 41. Persons having ordinary skill in the art have knowledge regarding running supply lines to the misting head from tank 10 and pump 30 through or about vertical strut system 57A, 57B and head strut system 41. Further, misting head 40 may be similarly mounted on curvaceous canopy strut 58. See FIG. 2.

Figure 4:
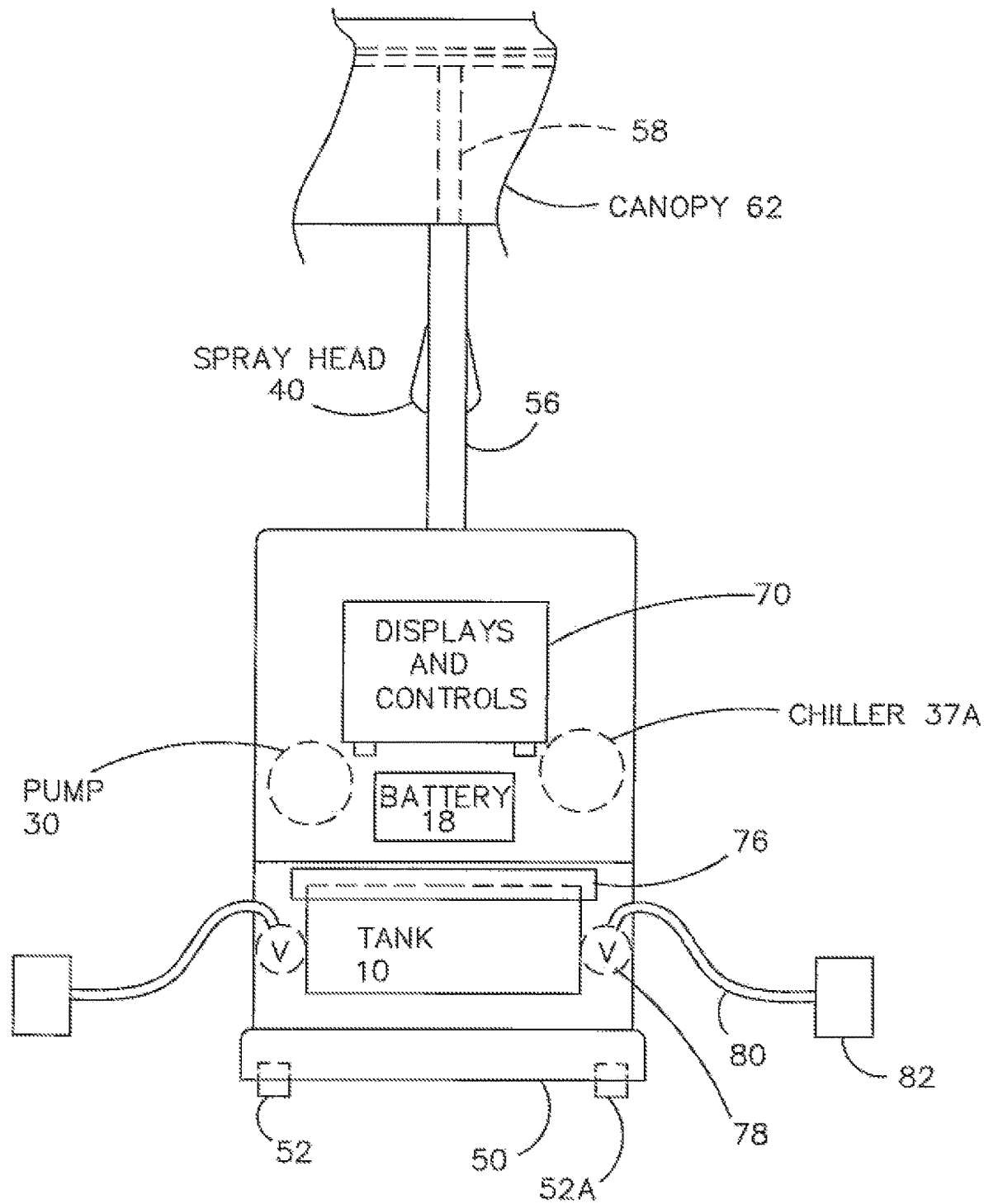
FIG. 4 diagrammatically illustrates a rear fragmentary view of the invention with the various optional features such as releasable couplings for sharing water supply when the misting system is configured as a modular system.

FIG. 4 diagrammatically illustrates a rear fragmentary view of the invention with the various optional features such as releasable couplings for sharing water supply when the misting system is configured as a modular system. More specifically, FIG. 4 shows chiller 37A as part of the hydraulic system. Tank 10 has lid 76 that can be removed or rotated such that the user or manager can load ice into the tank, thereby eliminating the need for chiller 37A. FIG. 4 also shows that the tank has hydraulic coupling element 80 terminating in a detachable coupler head 82 (normally CLOSED unless coupled) such that several modular misting seats can be joined together in a hydraulically coupled system as discussed later. Valve 78 is placed in an OPEN or ON position after tank 10 is hydraulically connected to the slaved misting modules. When the master misting module is not hydraulically coupled to a slaved misting module, valve 78 is CLOSED or in an OFF condition.

Figure 5:
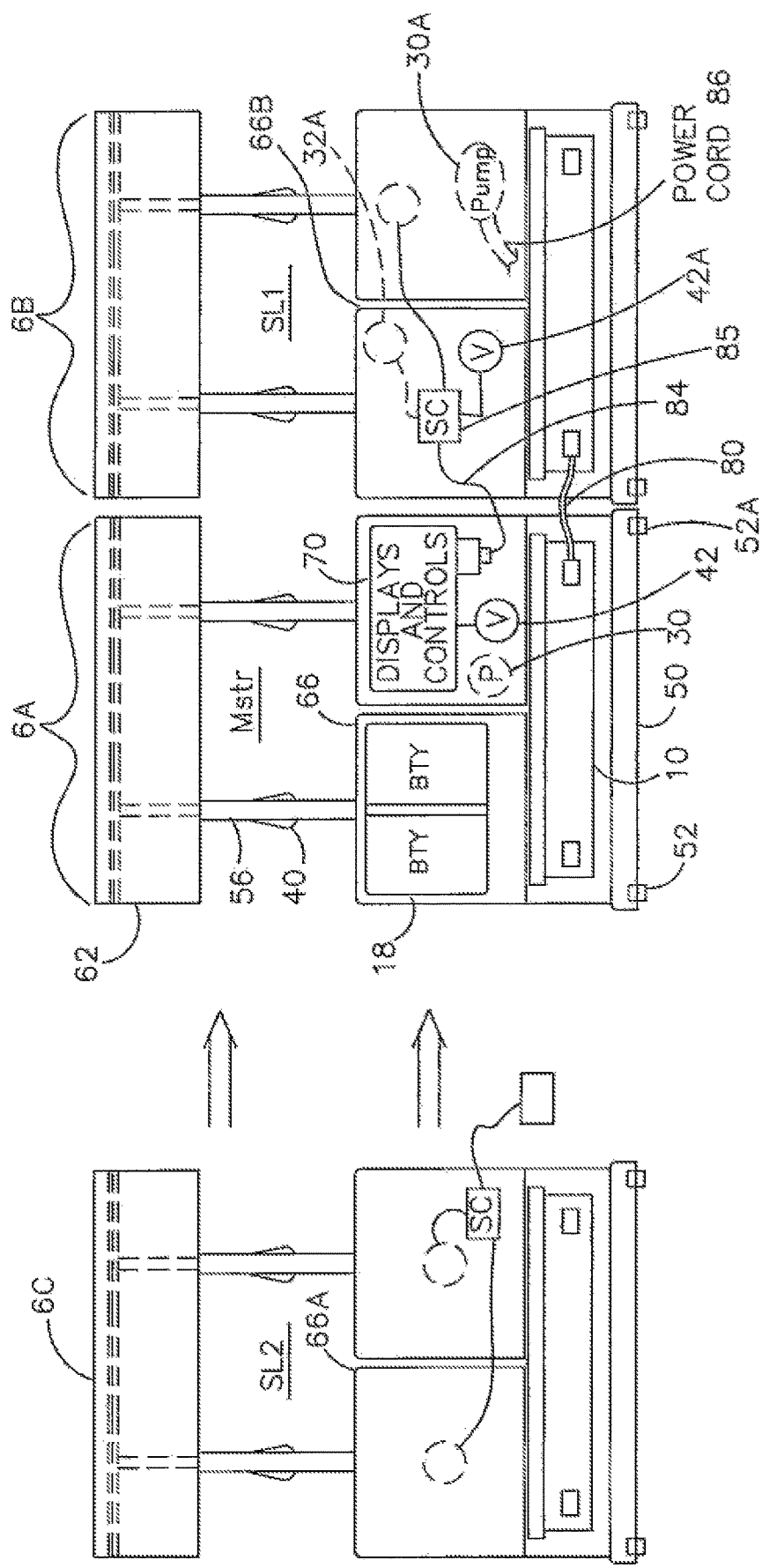
FIG. 5 diagrammatically illustrates the modular configuration of the misting system.

FIG. 5 diagrammatically illustrates the modular configuration of the misting system. In this illustrated embodiment, several two-seater misting modules 6A, 6B and 6C are shown. Master (mstr) module 6A includes one or more batteries 18 as an onboard power source. Also, master module 6A has a primary display and control system 70. Control lines 84 from display-control 70 are removably coupled to the appropriate hardware being controlled in the coupled slave module 6B. Likewise, water tank 10 in master module 6A is hydraulically coupled via detachable coupling line 80 to a slaved tank in slave module 6B. Alternatively, detachable hydraulic coupling line 80 may lead to water supply lines in the slave module 6B without the use of the illustrated separate water tank in slave module 6B. If the slave module has a water tank, then the water would be shared by both master module 6A and slave module 6B. In that sense, hydraulic line 80 and the detachable coupling should be near the bottom of the water tanks. In addition to the features described for the modular configuration discussed herein, the modular system may include mechanical coupling devices such that the master module can be attached mechanically to the slave module SL1 or SL2. In a similar sense, canopy 62 on the master module 6A can be a single, unitary piece with the canopy on slave module 6B (both canopy covers may consist of a single piece). Stated otherwise, once the mechanical coupling devices stabilize and join together each module 6A, 6B, 6C, the modular system may include a simple canopy. Also, a mechanical coupler may mechanically join the curvaceous canopy struts of modules 6A, 6B, 6C. In this construction, each module would have a curvaceous canopy strut at each lateral terminal end of canopy 62. The canopy mechanical couplers would join adjacent curvaceous terminal side canopy struts on module 6A to module 6B, and likewise join curvaceous terminal side canopy struts on module 6A to module 6C. Once the canopy struts are attached together by these couplers, a single piece canopy 62 can be deployed over the joined together canopy strut system. The single piece elongated canopy extending over modules 6A, 6B, 6C is then attached via the detachment systems discussed earlier in connection with the embodiment shown in FIG. 3. Independent modular mobility is permitted by disassembly of the mechanically and hydraulically interconnected modules 6A, 6B, 6C.

In a similar sense, if the modular misting system utilizes pressurized water initially developed by master pump 30 in master module 6A, then hydraulic line 80 would be coupled to the output of pump 30 which develops the pressurized water. Hydraulic line 80 would then be coupled to a slaved control valve 42A which controls the output of pressurized water to slaved misting heads in slave module 6B. In order to detect when a user has initially set down on a slaved seat in module 6B, slaved seat sensor 32A would be activated sending a slaved UA control command to controller 70. In a preferred embodiment, display-control system 70 primarily operates with digital controls. As such, control line 84 would be coupled in slave module 6B to a signal conditioner ("SC") 85. Likewise, seat sensor 32A would be coupled to a different signal conditioner SC since the control signals for slaved valve 42A and seat sensor 32A are typically different in a digital control system.

Alternatively, slave module 6B could include a slaved pump 30A which is supplied with detachable coupling power cord 86 to the onboard power supply on master module 6A. As known by persons of ordinary skill in the art, the control signal to slaved pump 30A could be (a) carried by the power supplied to the pump 30A or (b) be a separate control line to that pump.

Operationally, the modular system has a master UA control, either a manual control turned ON by the seated person or a UA seat sensor as described earlier. The slave UA control is also either a manual or a seat-sensitive UA control point. The canopies on the master and/or slave modules are releasably detachable. The modular system includes a master controller 70 electrically coupled to the pump and the master UA control 32 (all in the master module). The master controller 70 has a countdown timer function or a time-OFF clock function, to turn OFF the master pump control after an initial activation on time. This master pump control is generated by either the master UA control or the slave UA control. In this sense, the master controller 70 on the master module receives UA control commands from the seats on the master module and the seats on the slave module. For example, in a two-seater system (two seats on both the master and the slave modules), each seat having seat sensors, the master controller receives pump ON commands from any UA seat sensor. The same is true for the manual UA controls. However, once the pump is ON, the master controller 70 also controls the respective controllable valves interposed in corresponding supply lines and hence to the fluidly coupled misting heads. Once the pump is ON, the master controller senses which seat or UA control is activated ON, then commands the correct controllable supply line valve to OPEN, thereby misting the seated person in the seat. If only one person is seated, only that single supply line valve is OPEN and all others are CLOSED. Persons of ordinary skill in the art can design one-mister-for-one seat, multiple misters-ON-for-one-seat, one UA control ON for activating both misters wherein each seat has a mister head in a two-seater system, and various other configurations. The master module may detect the level of water in the mounted tank by a water level sensor. The master controller, in the master module, also includes a user display UD visually presenting a low water alert based upon the water level signal from the level sensor. The UD display may also show the ON-OFF misting condition of each seat in the multi-coupled modular system. One benefit of the modular system is that the electric power and main controls and UDs are on the master and the slave modules have only simple electronic controls (the sensor feedback command controls from the seat-mounted UA controls).

In FIG. 5, each seat in the two-seater modules has a vertical dividing panel 66, 66A, 66B. See FIG. 3. At a minimum, the master module 6A must include an onboard power source, batteries 18, and a water tank 10 and a display-control 70. The slave modules 6B and 6C may include or may not include a pump or a water tank dependent upon the configuration selected by the manufacturer. For example, a pressurized water system relies upon high-pressure hydraulic lines 80 being securely coupled between the master module 6A and the slave modules 6B, 6C. Multiple water tanks in both the master module and the slave modules enable the entire system to provide mist to many users over a longer period of time.

In a similar manner, the master onboard power supply can be supplemented by slaved power supplies (not shown) as needed by the designer. Again, the runtime for the entire module system is dependent upon the volume of water needed to cool the athletes or individuals involved in the athletic activity as well as the ambient temperature and the time span of the athletic events. In FIG. 5, slave module 6C has not yet been coupled to master module 6A but the arrows indicate potential coupling of slave module 6C to master module 6A. There are several benefits associated with the modular system. First, each module can be reduced in size, especially if the vertical strut is vertically collapsible, and the singular module can be placed in a truck or on a flat bed and be more easily transported to another venue or moved about the initial, primary sporting venue. Also, each module, when the tank is drained, can be moved by a single person by rotating the module onto the rearward pair of wheels 52, 52A and pulling the module about the venue (that is, pulling it indoors or about the field or playing pitch).

Figure 6:
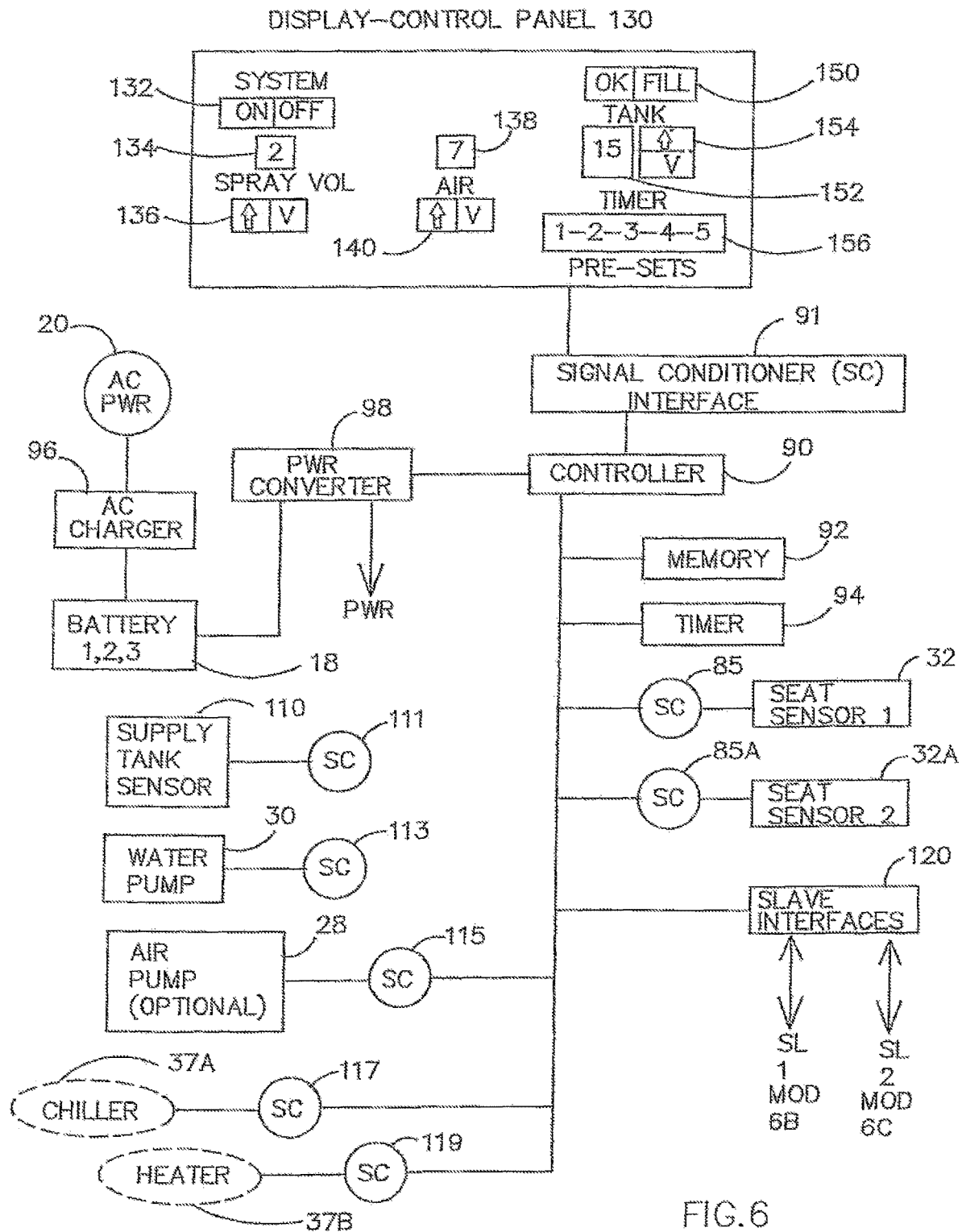
FIG. 6 diagrammatically illustrates one embodiment for electronic controls of the hardware, the display and the control panel.

FIG. 6 diagrammatically illustrates one embodiment for electronic control of the hardware, the display and the control panel. A person of ordinary skill in the art will understand that FIG. 6 describes functional aspects of a digital control system which may be greatly compressed with the use of specialized integrated circuits. Central to the illustrated embodiment of this digital control is a controller 90 which is a microcontroller. Signal conditioner SC 91 is electronically coupled to display-control panel 130. As known by persons of ordinary skill in the art, digital controls operate on lower voltages compared to power supplied to recharge battery 18. FIG. 6 shows AC power supply 20 is electrically coupled to AC charger 96 which in turn is electrically coupled to one or more batteries 18. Power is supplied to the digital control circuit from battery 18 via power converter 98. Digital power is represented by the schematic line connecting power converter 98 to controller 90. Power for various hardware is identified in FIG. 6 as PWR. Therefore, PWR is supplied to water pump 30 and, if utilized, air pump 28.

Controller 90 is electronically connected to memory 92 and timing circuit 94. It is known by persons of ordinary skill in the that controller 90 may be an integrated circuit with functional modules such as a countdown timer and a clock. Controller 90 is coupled to various hardware components via signal conditioners SC 111, 113, 115, 85, 85A and 91. Persons of ordinary skill in the art well recognize that some of the signal conditioner SC circuits may be integrated into microcontroller 90 dependent upon the selected hardware to be controlled and the type of microcontroller. Controller 90 is also electronically coupled to slave interfaces 120 which lead to slave modules 6B (SL1)

and slave module 6C (SL2) when the respective control lines are electronically joined to the master controller 90 on the master module 6A.

FIG. 6 diagrammatically illustrates display-control panel 130 as an example. The invention may have various types of display-control panels including touch-sensitive control panels, display panels with independent LED displays or combinatory led displays (actuated when the user selects a particular control feature), manual switches, touch sensitive switches, knobs, and button control features. Therefore, the display-control panel illustrated in FIG. 6 is just one of many types of display-control panels available. Also, the display panel may be separate and apart from the controller. Potentially, the display control may be a separate tablet which is network-coupled to a master controller 90.

The exemplary display-control panel 130 includes a system ON-OFF control and a user/manager display (UD) indicator 132 showing that the system is ON or OFF, a spray volume or spray intensity control 136 and an associated UD display 134. For example, in FIG. 6, the UD displayed volume is set at low level "2" (indicia 134) (wherein the maximum level is, by example, "9") and the user/manager actuated display-control 136 can increase the spray volume by selecting the up arrow or decrease the spray volume by selecting the down arrow (shown as a "V"). In a similar manner, if an air pump is utilized, and air pump level is shown in UD display 138 and the user/manager actuated UA controls the air pressure with the up arrow or down arrow controls 140 (down arrow shown as a "V"). The user/manager UD display 150 indicates that the water tank contains a reasonable amount of water as indicated by the "OK" water indicator and further indicates the need to fill the water tank by a "FILL" display in display region 150.

In this example, the controller 90 has a time out function represented by timer 94 such that once the seat sensor 32 is activated ON a particular misting module, the controller turns ON the pump activating the production of mist onto the user seated in the misting module for a predetermined period of time. In this illustrated example, the controller activates the misting module for a preset time of "15" minutes, as shown in UD display region 152. The user/manager, by actuating user actuatable UA control 154 can manually increase or decrease the time by actuating the exemplary up arrow or down arrow control in the dual control set 154 and thus, increase or decrease the misting system ON, resulting in delivery of mist once activated ON by a seated user/athlete on UA seat control 54. Control sets 136, 140 and 154 show up arrows and down arrows ("down" referenced by a "V"). The result being the misting control, which is coupled to the UA control and a user/manager input control 154, enables the user/manager to input control data representing the event time and the misting controller thereby limiting the ON-time misting periods to ensure that the water supply is adequate for the athletic event and at least for the event time.

Also, the controller 90 may permit the user/manager to pre-set certain time-ON periods. This is represented by the pre-sets 1, 2, 3, 4, and 5 in UD display 156. A more sophisticated control system would permit the user/manager to input the time duration of the athletic events via a UA control and use an algorithm to decrease the ON-time period of each misting station once that UA seat station has been activated by the user/athlete. Further enhancements would include monitoring the ambient temperature and/or the ambient humidity, factoring in the preprogrammed length of time of the athletic activity and decreasing the ON-time period of each misting station to ensure that the misting stations operate at least through the end of the athletic event given pre-set ambient temperatures and/or humidity levels. Higher temperatures/humidity shortens the ON-time misting periods whereas lower temperature/humidity lengthens the ON-time misting periods. Artificial intelligence may be incorporated in the controller 90 and memory 92, along with ambient temperature sensors and ambient humidity sensors to enhance the operation of the system. As an example, a higher ambient temperature would automatically shorten the ON-time periods of the misting stations. The same is true regarding higher ambient humidity readings. The AI control or a simple time-based function control could monitor "seat-time" of all user/athletes currently using the misting system, and limit the ON-time misting periods to ensure that the misting system water supply is adequate for the entire athletic event. In other words, the "time-in-seat" indicates a higher misting usage mandating less misting ON times per athlete whereas lower "time-in-seat" indicates longer misting ON times. Integrating ambient temperature and humidity data during the event with the time-in-seat data results in an efficient use of the limited power and/or water supply. With a properly trained AI system, the AI system would have data tables in memory 92 accounting for misting volume, electrical on-board power reserves and power utilization data for the pump (and possibly the chiller). The AI algorithm then calculates misting ON times to match power, water, and real-time athlete utilization.

Figure 7:
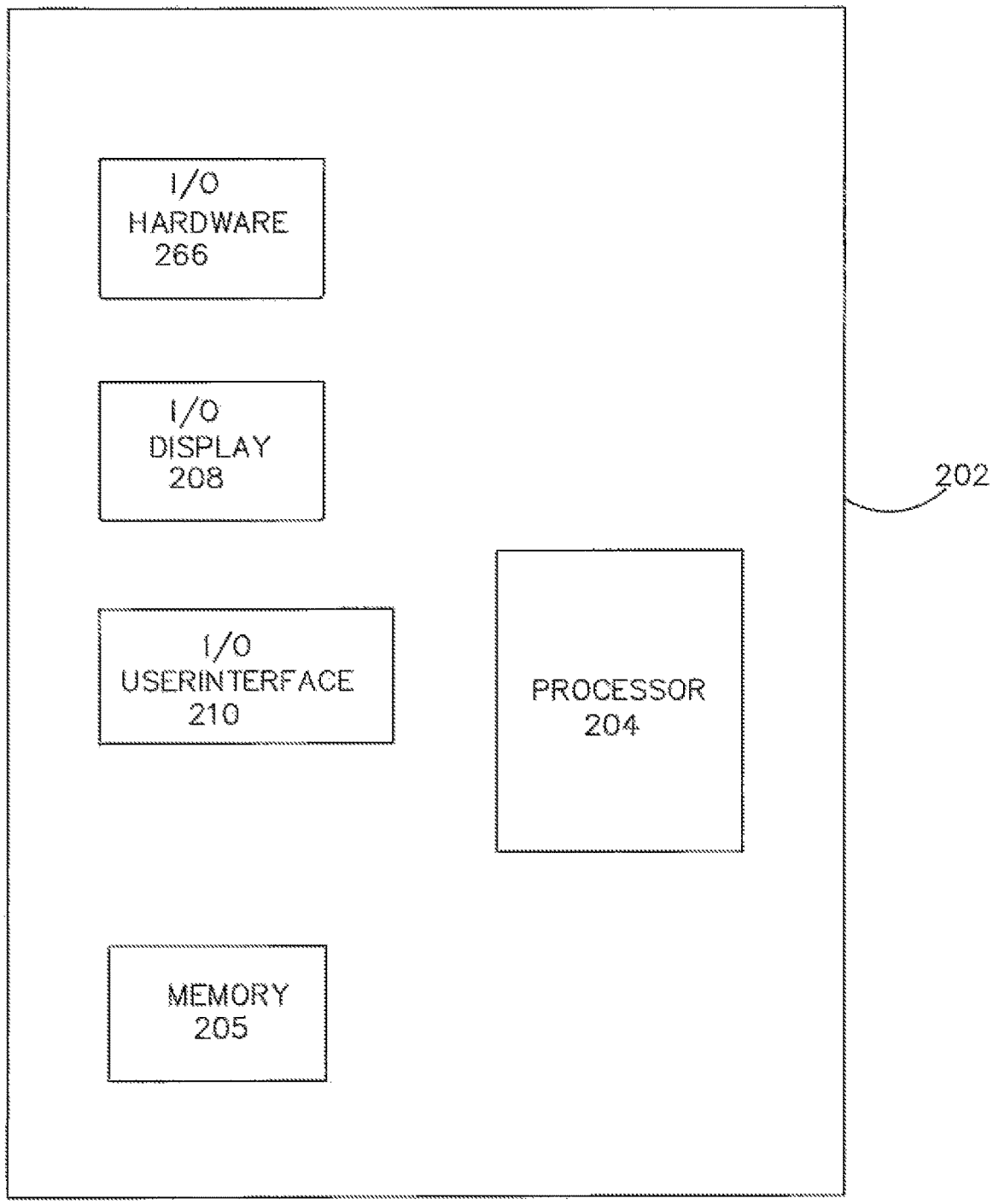
FIG. 7 diagrammatically illustrates a high-level electronic control and monitoring system for the present invention.

FIG. 7 diagrammatically illustrates a high-level electronic control and monitoring system for the present invention. For example, control system 202 may be completely digital in nature and may include an operator interface deployed as an App on a smartphone or a tablet, a compact controller 202 mounted in the master module (or stand-alone module) in communications with the App and various communications interfaces (such as near-field BLUETOOTH communication links). A cloud-based system is also encompassed by an embodiment of this invention. The smartphone or tablet could be in communication with the onboard digital controller 90 which is supported by the master misting module. Processor 204 encompasses the concept of utilizing the processor in the smartphone or tablet as well as the processor on the master module. Input/output hardware functions 206 control the hardware discussed earlier, that is, the pump, valves and water level controls and output via the onboard processor 90. Input/output display(s) 208 represent functions that can be displayed and controlled on the smartphone or tablet which control-command displays show the condition of each misting module, water reserves, mist output, misting time limits, as well as how often an athlete is seated at a misting station. Input/output for the user interface (UI) 210 is also a combination of the App on the smartphone or tablet as well as the onboard processor on the master misting station. Processor 204 operates in conjunction with memory 205.

The claims appended hereto are meant to cover modifications and changes within the scope of the present invention.

The invention claimed is:
1. A modular misting system comprising:
 a master misting module and a slave misting module removably coupled to the master module;
 the master module having:
  a master seat supported by a master platform, the master seat adapted to provide seating for a corresponding person subject to aerosolized water released above and about the master seat;

a water tank supported by the master platform and a pump fluidly coupled to the tank controlled by a master pump control;

an electrical power source coupled to the pump and supported by the master platform;

a water supply line coupled at one end to an output of the pump and at an opposite end to an aerosolizing misting head;

a master controllable valve in the water supply line controlled by a master valve control;

a canopy mounted above the master platform by at least one vertical strut element and at least one over-master seat strut element, the at least one over-master seat strut element extending above and partly over the master seat;

the misting head and the supply line mounted on either the at least one over-master seat strut element or the at least one vertical strut element;

a master user actuated (UA) control on or adjacent to the master seat and electrically coupled to the pump and the master valve, the master UA control activating the pump ON with the master pump control and activating the master valve control OPEN when the UA control is activated ON by the corresponding person thereby releasing aerosolized water over the master seat;

the slave module having:

a slave-mounted seat supported by a slave platform providing seating for a respective person subject to aerosolized water released above and about the slave-mounted seat;

a slaved water supply line having a slaved input at one end and at an opposite end to a slaved aerosolizing misting head;

a slaved controllable valve in the slaved supply line controlled by a slaved valve control;

a second canopy mounted above the slave platform by a corresponding at least one vertical strut element and a corresponding at least one over-slave seat strut element, the corresponding at least one over-slave seat strut element extending above and partly over the slave-mounted seat;

the slaved misting head and the slaved supply line mounted on either of the corresponding at least one over-slave seat strut element or the corresponding at least one vertical strut element;

a slaved UA control on or adjacent to the slave-mounted seat, the slaved UA control activating the pump ON with the master pump control and the slaved valve control OPEN when the slaved UA control is activated ON by the respective person in the slave-mounted seat, and, in the absence of any respective person in the slaved-mounted seat, either the slaved UA control or the master UA control activating the slaved valve control CLOSED;

wherein the master module and the slave module are coupled together by (i) a detachable water line coupler between the pump and the salved water supply line, and (ii) a detachable control line coupler from the slaved UA control.

2. The misting system as claimed in claim 1 wherein either (a) the master UA control is either (i) a manual control adapted to be turned ON by the corresponding person seated in the master seat, or (ii) a seat sensor activated by the respective corresponding person seated in the master seat; or (b) the slave UA control is either (i) a manual control adapted to be turned ON by the respective person seated in one of the slave-mounted seat, or (ii) a seat sensor activated by the respective person seated in the two slave-mounted seat.

3. The misting system as claimed in claim 2 including a removable master canopy and a removable slave canopy and wherein one or the other or both of the master module or the slave module include a plurality of manually releasable detachment mechanisms intermediate the one or the other or both the master or slave removable canopy and the at least one over-master seat or over-slave seat strut element, wherein the manually releasable detachment mechanism is one from the group of a snap, a hook and loop, a button and a complementary button hole, fabric clothes having micro hooks cooperative with complementary micro loops, a fabric tether, a tongue operative in a groove, a strap, and a tie down.

4. The misting system as claimed in claim 1 wherein the electrical power source is one of a rechargeable battery, a solar panel coupled to a complementary battery, and a removable rechargeable battery movably mounted in a battery containment.

5. The misting system as claimed in claim 1 wherein the master module has two master seats which are conjoined, the slave module as two slave-mounted seats which are conjoined, and the master platform and the slave platform each includes at least a pair of wheels rotatably mounted thereon, providing a modular, movable misting system.

6. The misting system as claimed in claim 1 wherein the master module includes a water chiller in the water supply line.

7. The misting system as claimed in claim 6 including a master controller electrically coupled to the pump and the master UA control, the controller having a countdown timer function to turn OFF the master pump control after an initial activation of the master pump control ON, and the controller having a chiller ON function dependent upon the initial activation of the master pump control ON and a chiller OFF function dependent upon a chiller countdown timing function.

8. The misting system as claimed in claim 7 wherein a water level sensor in the tank generating a water level signal, the controller being electrically coupled to the water level sensor and obtaining the water level signal, the controller having a user display (UD) interface visually presenting a low water alert based upon the water level signal.

9. The misting system as claimed in claim 1 wherein the pump having a pressure pump control to maintain a predetermined pressure in the downstream water supply line.

10. The misting system as claimed in claim 9 the pump is actuated ON when the pressure pump control senses less than the predetermined pressure in the downstream water supply line and either (a) the master UA control is actuated ON or (b) the slaved UA control is activated ON or (c) both the master UA control and the slaved UA control is activated ON.

* * * * *